(12) United States Patent
Fisher et al.

(10) Patent No.: US 6,790,185 B1
(45) Date of Patent: Sep. 14, 2004

(54) SEALANT PLUG DELIVERY METHODS

(75) Inventors: John S. Fisher, Belleair, FL (US); Frederick Ahari, Tucson, AZ (US)

(73) Assignee: Biopsy Sciences, LLC, Clearwater, FL (US)

( * ) Notice: Subject to any disclaimer, the term of this patent is extended or adjusted under 35 U.S.C. 154(b) by 15 days.

(21) Appl. No.: 10/248,261

(22) Filed: Dec. 31, 2002

(51) Int. Cl.$^7$ .............................................. A61B 10/00
(52) U.S. Cl. ...................................................... 600/562
(58) Field of Search ................................ 600/562, 564, 600/566, 567, 565, 576; 604/131, 164.06, 164.13, 15, 264, 265; 606/213; 128/DIG. 8

(56) References Cited

U.S. PATENT DOCUMENTS

| | | | | |
|---|---|---|---|---|
| 4,791,937 A | * | 12/1988 | Wang | 600/565 |
| 5,487,392 A | * | 1/1996 | Haaga | 600/566 |
| 5,718,237 A | * | 2/1998 | Haaga | 600/564 |
| 6,071,301 A | * | 6/2000 | Cragg et al. | 606/213 |
| 6,086,607 A | * | 7/2000 | Cragg et al. | 606/213 |
| 6,280,399 B1 | * | 8/2001 | Rossin et al. | 600/567 |
| 6,447,534 B2 | * | 9/2002 | Cragg et al. | 606/213 |

* cited by examiner

Primary Examiner—Mary Beth Jones
Assistant Examiner—Brian Szmal
(74) Attorney, Agent, or Firm—Ronald E. Smith; Smith & Hopen, P.A.

(57) ABSTRACT

A bioabsorbable sealant plug that expands in response to contact with moisture in a mammalian body is optimally positioned in a biopsy tract to seal the biopsy tract when a biopsy procedure is completed. In a first method, the leading end of the sealant plug is advanced through the lumen of a coaxial needle by a plunger until a leading end of a supporting leg abuts the patient's skin surface. A second method is performed with a pistol-shaped tool having a trigger that enables adjustment of the plunger. A third embodiment includes a plunger having a bifurcated end that grasps the plug. A fourth embodiment has a turning nut that causes compression of a gasket that clamps down on the plug. A supporting rod and coaxial needle are in parallel relation to one another in a fifth embodiment.

13 Claims, 12 Drawing Sheets

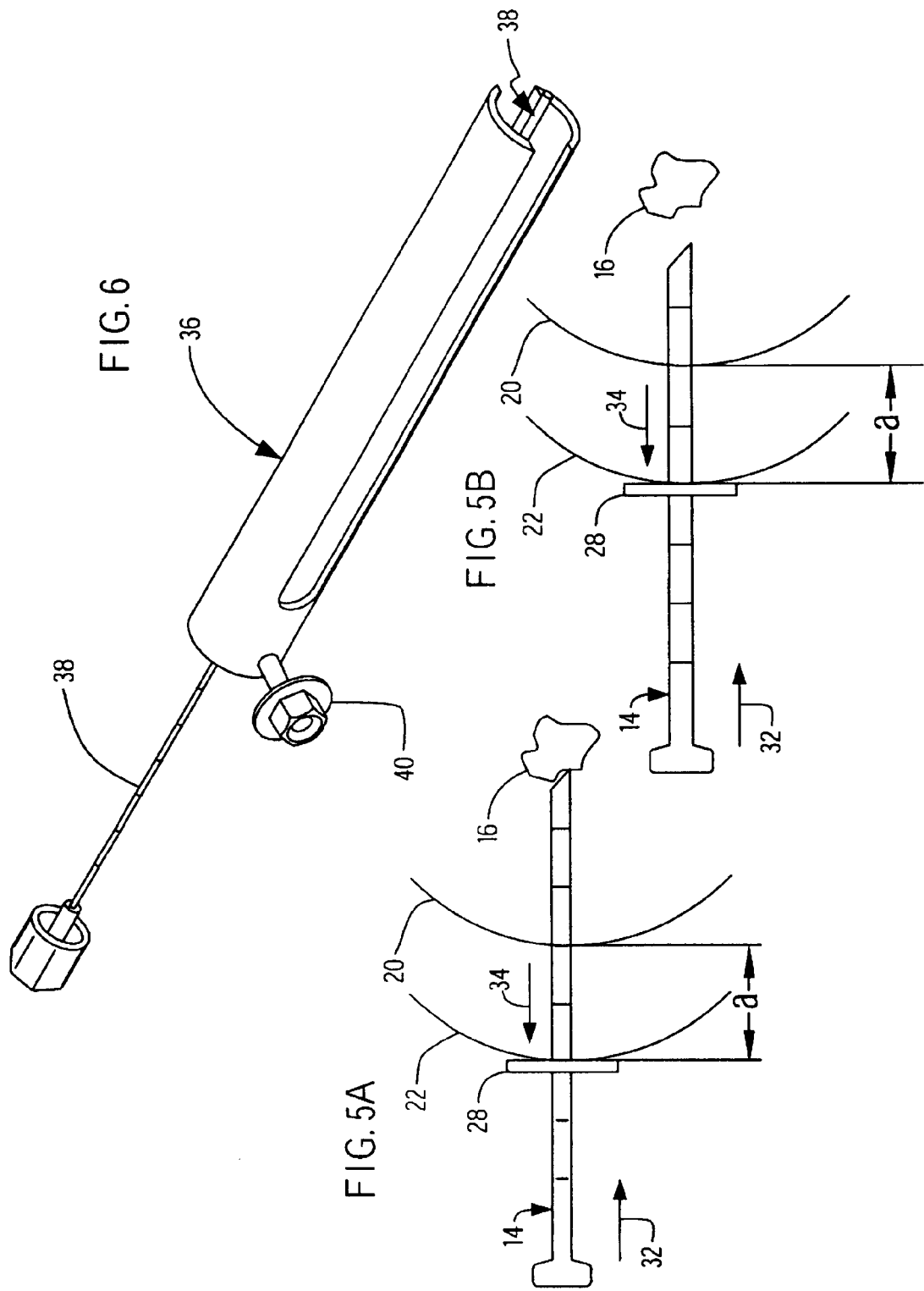

| a (cm) | Plunger/Support leg Settings |
|---|---|
| 0 | Adjust to 10th notch |
| 0-.5 | adjust to 9th notch |
| .5-1 | adjust to 8th notch |
| 1-1.5 | adjust to 7th notch |
| 1.5-2 | adjust to 6th notch |
| 2-2.5 | adjust to 5th notch |
| 2.5-3 | adjust to 4th notch |
| 3-3.5 | adjust to 3rd notch |
| 3.5-4.0 | adjust to 2th notch |
| 4.0-4.5 | adjust to 1st notch |

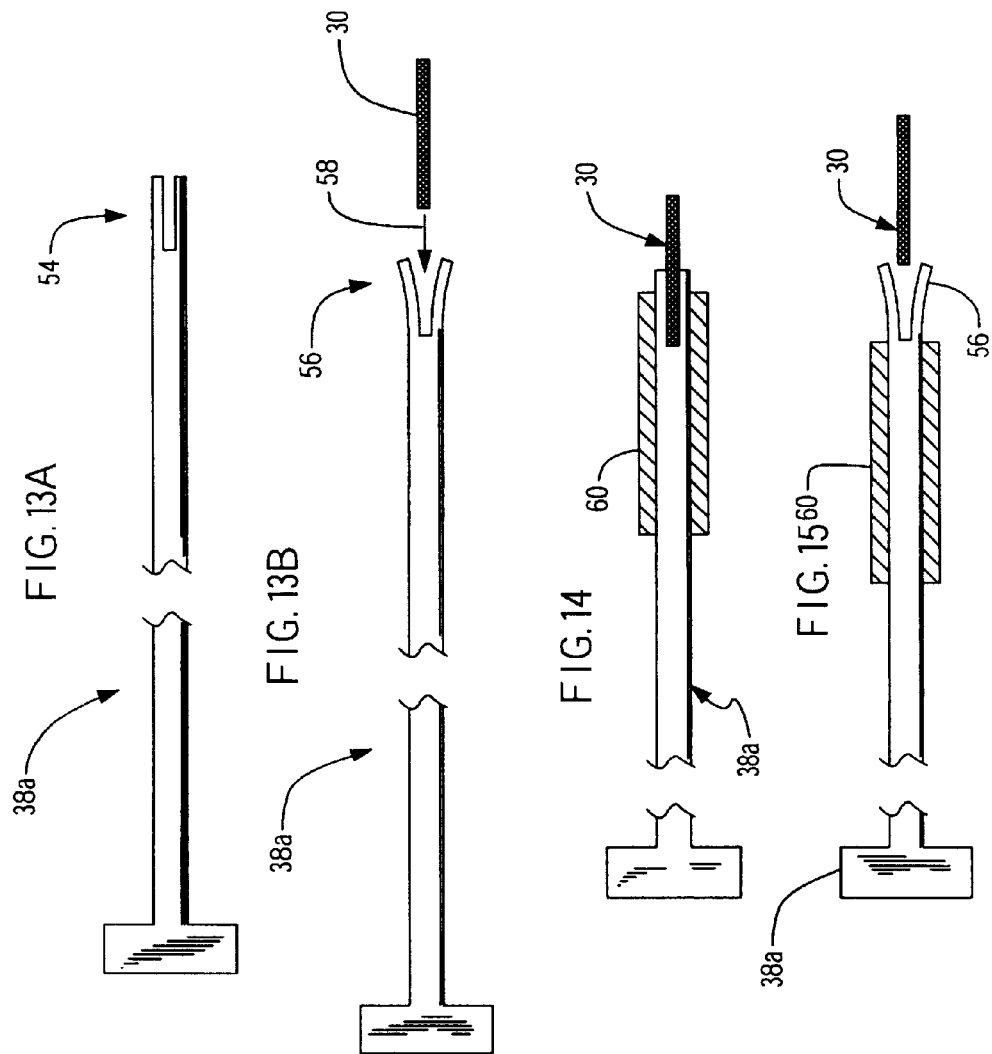

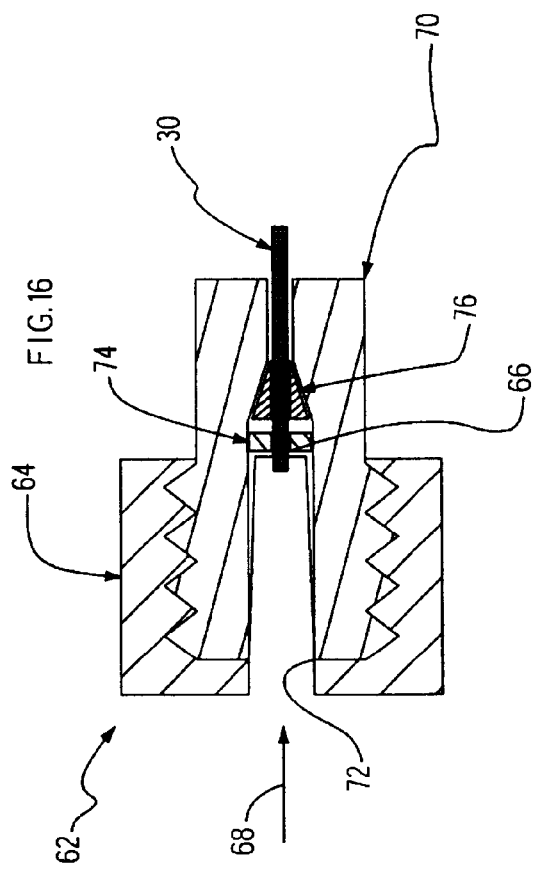
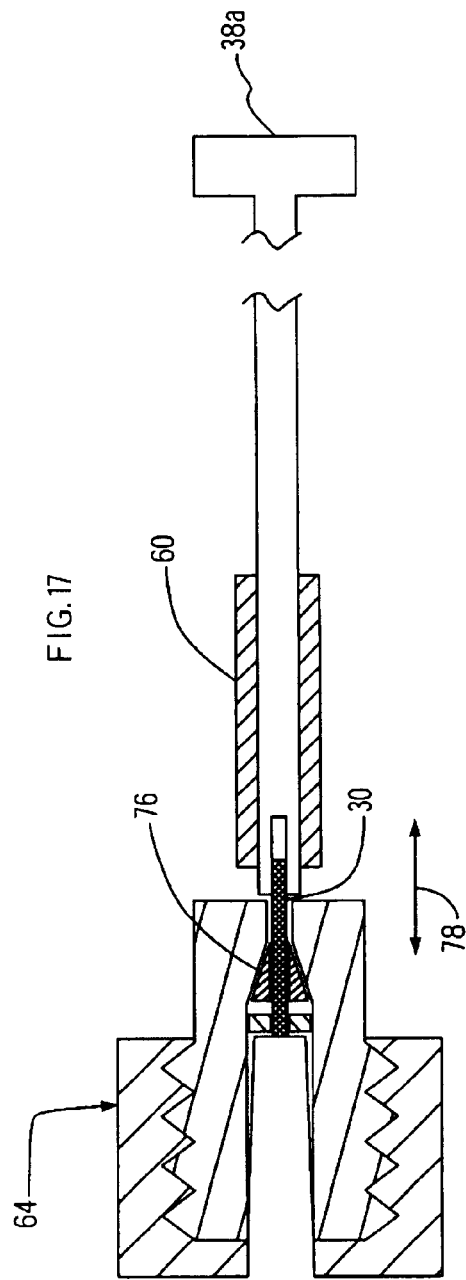

SEALANT PLUG DELIVERY METHODS

BACKGROUND OF INVENTION

1. Field of the Invention

This invention relates, generally, to methods for sealing biopsy tracts. More particularly, it relates to apparatus and methods that enable precise positioning of a bioabsorbable sealant plug in a predetermined optimal location.

2. Description of the Prior Art

Air leaks commonly occur at pulmonary tissue sites that have been dissected during surgical resection and manipulation or surgical resection or manipulation. Air leaks also occur after fine needle aspiration biopsy of the lung. Pneumothorax (air leakage) occurs in about thirty per cent (30%) of lung biopsies. An opening in a lung is undesirable because air leaks therefrom and causes the lung to collapse. Openings in other organs, such as the heart, liver, kidney and the lime are also undesirable due to excess bleeding and other related problems.

Pending patent application Ser. No. 10/063,620, filed May 6, 2002 by the present inventors discloses a novel hydrogel polymeric base material formed into the shape of a plug to seal a biopsy tract to prevent pneumothorax in the lungs and bleeding in other internal organs. That pending patent application is incorporated by reference into this disclosure.

There remains a need, however, for apparatus and methods for accurately delivering the sealant plug under CT imaging and other imaging modalities and deploying it with a high degree of precision to achieve optimal efficacy.

The sealant plug must be placed beyond the pleura of the lung to prevent pneumothorax. Accurate placement is required for any depth and position of the biopsy or tissue tract. Such accurate placement must also be made for other internal organs such as the liver, kidney, the heart, i.e., the sealant plug must be positioned at or beyond the surface of such organs to prevent or eliminate bleeding.

There is also a need for a sealant plug having a faster rate of hydration than the plugs heretofore known. One of the most important parameters of a sealant plug is the expansion rate and its ability to seal a tract in a short period of time.

A sealant plug is needed that provides a faster expansion rate than the sealant plugs heretofore known so that it will seal a tract faster, thereby reducing pneumothorax in a lung and bleeding in other internal organs.

However, in view of the prior art considered as a whole at the time the present invention was made, it was not obvious to those of ordinary skill in the pertinent art how such apparatus and methods and improved sealant plugs could be provided.

SUMMARY OF INVENTION

The long-standing but heretofore unfulfilled need for a delivery system for accurately placing a bioabsorbable sealant plug in an optimal location in a biopsy tract is now met by a new, useful, and nonobvious invention. The novel method includes the steps of performing a biopsy procedure with a biopsy needle and a coaxial needle having a movably mounted marker thereon. When the biopsy procedure is finished, the biopsy needle is removed from a biopsy tract formed by the procedure. The coaxial needle is left in the biopsy tract in the same position it was in during the biopsy procedure.

A distance "a" is measured by an imaging means from a point of entry by the biopsy needle at a skin surface to the surface of the internal organ upon which the biopsy procedure was performed.

A distance "b" is measured by the imaging means from the surface of the internal organ at the point of entry to a lesion within the internal organ.

Where a sealant plug of cylindrical configuration having a preferred length of about two and one-half centimeters (2.5 cm) is used, a distance "d" is calculated by adding two centimeters (2.0 cm) to distance "a." If a plug having a length of 1.5 cm is used, distance "d" is calculated by adding 1.0 cm to distance "a." If a plug having a length of 3.0 cm is used, distance "d" is calculated by adding 2.5 cm to distance "a." The distance added to distance "a" must position the leading end of the plug at a depth in the biopsy tract such that about one-half centimeter (0.5 cm) of the trailing end of the plug protrudes out of the biopsy tract, beyond the surface of the lung or other internal organ, for a plug of any length. Thus, half a centimeter is subtracted from the length of the sealant plug, and that length is added to distance "a" to arrive at distance "d." After the biopsy procedure has been completed and the biopsy needle has been removed from the lumen of the coaxial needle and distance "d" has been calculated, the coaxial needle is advanced or retracted as needed so that its distal end is distance "d" from the surface of the patient's skin. Centimeter markings or graduations are imprinted, notched, or otherwise marked on the coaxial needle, beginning from its distal end.

More particularly, suppose a plug of length 2.0 cm is used and distance "d" is therefore calculated by adding 1.5 cm to distance "a" so that the trailing end of the plug will protrude from the biopsy tract by 0.5 cm when the plug is properly positioned. If distance "a" is 3.0 cm, then distance "d" is equal to 4.5 cm. If the distal end of the coaxial needle is less than 4.5 cm from the surface of the patient's skin at the conclusion of the biopsy procedure, the marker on the coaxial needle is moved to the 4.5 cm position and the coaxial needle is advanced until the marker abuts the patient's skin. If the coaxial needle is more than 4.5 cm beneath the patient's skin at the conclusion of the biopsy procedure, the marker is moved back if needed and the coaxial needle is withdrawn until the 4.5 cm marker thereon is flush with the patient's skin and the movable marker is then brought into contact with the patient's skin.

A supporting leg and a plunger are then connected to one another and their respective positions relative to one another are adjusted in accordance with a chart containing predetermined settings including a plunger-to-supporting leg ratio with respect to measurement of said distance "a." Graduation markers on the plunger are provided to facilitate the interconnection. The plunger is then locked into position relative to the supporting leg, thereby forming a plunger/supporting leg assembly.

The sealant plug is then introduced into the coaxial needle at the trailing end thereof. The assembly is then brought into ensleeving relation with the coaxial needle. Specifically, the leading end of the supporting leg is positioned in abutting relation to the patient's skin. The leading end of the plunger enters into the trailing end of the lumen of the coaxial needle, pushing the sealant plug ahead of it in a trailing-to-leading direction. When the leading end of the supporting leg abuts the patient's skin, the sealant plug is still housed within the lumen of the coaxial needle, but it is positioned at the desired position. Specifically, the leading end of the sealant plug is flush with the leading end of the coaxial needle.

The coaxial needle is then removed from the biopsy tract while maintaining the supporting leg and the plunger in their respective positions, thereby deploying the sealant plug into the biopsy tract. The trailing 0.5 cm of the sealant plug protrudes from the biopsy tract, above the surface of the internal organ having the lesion that was the subject of the biopsy. The supporting leg and the plunger are then withdrawn, leaving the sealant plug in said internal organ at said preselected optimal position.

In a second embodiment, the method for delivering a sealant plug to an optimal position within an internal organ with a high degree of accuracy includes the steps of providing a supporting leg in the form of a pistol grip body that includes a pivotally-mounted trigger. A plunger is mounted to the supporting leg such that the plunger may be advanced or withdrawn when the trigger is pulled. A marker is slideably mounted on the plunger and graduation marks are provided along the extent of said plunger. Graduation marks are also are imprinted or otherwise provided along the extent of the supporting leg.

As in the first embodiment, distance "a" is determined and a distance "d" is calculated by adding to distance "a" a distance, in centimeters, that is 0.5 cm less than the length of the sealant plug in centimeters. A marker is used as in the first embodiment to denote the desired depth and the distal end of the coaxial needle is positioned at said depth.

With the trigger pulled to allow movement of the plunger, the plunger and the supporting leg are positioned relative to one another as determined by a setting provided by a chart as in the first embodiment, and locked together to form an assembly by releasing the trigger. The positioning is performed by aligning a graduation mark on the plunger with a graduation mark on the supporting leg in accordance with said chart.

A sealant plug is then introduced, using a suitable holding tool, into the lumen of the coaxial needle at the trailing end thereof and the plug is pushed in a trailing-to-leading direction with a leading end of the plunger until the leading end of the supporting leg abuts the patient's skin as in the first embodiment. The sealant plug is then positioned within the coaxial needle such that the leading end of the sealant plug is flush with the leading end of the coaxial needle. The coaxial needle is then withdrawn from the internal organ and from the patient's body while maintaining the position of the plunger. The plunger/supporting leg assembly is then removed and optimal positioning of the sealant plug is thereby obtained.

A third method for delivering a sealant plug to an optimal position within an internal organ with a high degree of accuracy includes the steps of providing a plunger in the form of a tube having a slot formed in its distal end so that the distal end is bifurcated into two arm members. An inside diameter of the tube is configured so that the inside diameter is smaller than an outside diameter of the sealant plug. The plunger is formed of a flexible and resilient material with memory so that the arms may be spread apart from one another. The arms are spread apart from one another and a trailing end of the sealant plug is positioned between the open arms. The tube is ensleeved in a sleeve member and the sleeve member is advanced in a trailing-to-leading direction, thereby causing the arms to close with respect to one another. Thus, the arms clamp down on the sealant plug. The sealant plug is positioned at a predetermined optimal position by following the steps of the first two embodiments and the sleeve member is retracted so that the arms spread apart from one another under their inherent bias, thereby releasing the sealant plug at the optimal position. The plunger and sleeve member are then withdrawn, leaving the sealant plug in the optimal position.

A fourth method for delivering a sealant plug to an optimal position within an internal organ with a high degree of accuracy includes the step of providing a cylindrical housing having screw threads formed on an external surface thereof and having a longitudinally-extending throughbore formed therein. A screw-threaded turning nut screw-threadedly engages the screw threads formed in the external surface of the cylindrical housing. The turning nut has a central hub that includes a leading end that extends into a trailing end of the bore formed in the cylindrical housing. A centrally apertured flat washer is positioned in leading relation to the leading end so that the flat washer is constrained to displace in a trailing-to-leading direction when the turning nut is advanced. A flexible and resilient gasket of frusto-conical configuration and having a central throughbore formed therein is positioned in leading relation to the flat washer so that the flexible and resilient gasket is also constrained to displace in a trailing-to-leading direction when the turning nut is advanced. A diameter-reducing taper is formed in the longitudinally-extending throughbore so that the throughbore has a reduced diameter leading end. The turning nut is advanced so that the leading end thereof bears against the flat washer and the flat washer bears against the trailing end of the flexible and resilient gasket, thereby driving the gasket into the reduced diameter leading end of the throughbore. The diameter-reducing taper serves to gradually compress the flexible and resilient gasket into the reduced diameter leading section as the turning nut is advanced. The trailing end of the sealant plug is positioned within the central aperture of the flat washer and the central throughbore of the flexible and resilient gasket so that the trailing end of the sealant plug is compressed as the flexible and resilient gasket is driven into the reduced diameter bore, thereby locking down on that part of the sealant plug disposed within the flat washer central aperture and central bore of said flexible and resilient gasket.

A fifth method for delivering a sealant plug to an optimal position within an internal organ with a high degree of accuracy includes the step of positioning a coaxial needle at a predetermined depth by employing an imaging means to determine a distance between a patient's skin surface and the surface of an internal organ just as in the earlier embodiments.

A positioning adaptor is provided and a supporting rod and a coaxial needle are interconnected to one another with the positioning adaptor to guide the supporting rod with respect to the coaxial needle. A supporting adaptor is provided for interconnecting the supporting rod and a plunger to one another. The supporting adapter is locked to the supporting rod. The relative positioning of the supporting rod and the plunger are adjusted based upon a chart as in the earlier embodiments, and the supporting rod and plunger are locked into position. A sealant plug is introduced into the lumen of the coaxial needle, at the trailing end thereof as in the other embodiments, and the plunger is advanced in a trailing-to-leading direction through said lumen, pushing the sealant plug in front of it until the leading end of the supporting rod abuts the patient's skin, thereby stopping the trailing-to-leading travel of the plunger as in the earlier embodiments. The supporting rod has a flat, atraumatic distal end that rests against the surface of the skin without imparting trauma thereto. As in the earlier embodiments, the leading end of the sealant plug is flush with the leading end of the coaxial needle when the leading end of the supporting rod abuts the patient's skin. The supporting rod and plunger are held in place while the coaxial needle is withdrawn from the biopsy tract. The plunger/supporting rod assembly is then withdrawn, leaving the sealant plug optimally positioned in the biopsy tract. i.e., with its trailing end protruding from the outer surface of the internal organ by a distance of about 0.5 cm.

Different dehydration techniques and different shapes and sizes have some effect on the expansion rate of a sealant plug. Another method of changing the expansion rate of the materials disclosed in the incorporated patent application is to induce stress in the polymer. A smaller in size stress induced sealant plug could be used in applications where more dwell time is needed during delivery and where a faster expansion rate is required after deployment. Stress may be introduced in three different forms:

1. During the dehydration process;
2. After the dehydration process; and
3. During delivery and deployment of a sealant plug using a unique delivery system.

A method of pre-stressing a dehydrated sealant plug so that it hydrates at a faster rate than a dehydrated sealant plug that has not been pre-stressed includes the steps of grasping a first end of the sealant plug with a first holder, grasping a second end of the sealant plug with a second holder, and separating the holders from one another to apply tension to the sealant plug.

The amount of stress is correlated with the expansion rate of the sealant plug. The stress can be induced gradually by pulling, pushing, compressing, rotating or otherwise momentarily deforming the sealant plug during the dehydration process. This is most efficiently achieved by special fixturing and machinery.

The stress may also be induced by the same techniques after the dehydration process is completed. Stress can be induced from one per cent (1%) to ninety-nine per cent (99%), but the working range is between twenty-five per cent (25%) to seventy-five per cent (75%). One of the methods is to stretch the dehydrated sealant plug by pulling it using special fixtures. Other methods include compression force and torque applied to the sealant plug. Expansion rates of two to five times faster than unstressed sealant plugs may be achieved by this method. Optimum results have been achieved by providing two (2) to three (3) times the expansion rate due to fifty per cent (50%) induced stress.

A delivery system that can stretch a sealant plug before or during delivery may also induce expansion rate-enhancing stress.

An important object of this invention is to provide an apparatus for delivering and deploying a bioabsorbable sealant to a predetermined optimal location in a biopsy tract with a high degree of accuracy.

Another major object is to teach the art an ideal sealant plug deployment.

Another object is to achieve optimal efficacy by providing a sealant plug having a rate of hydration that is faster than the sealant plugs of the prior art while providing a smaller implant.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 5A is a diagrammatic, side elevational view of a coaxial needle in position for a biopsy procedure;

FIG. 5B is a diagrammatic, side elevational view of the coaxial needle of FIG. 5A after the biopsy procedure has been completed and the coaxial needle has been withdrawn one centimeter because a 2.5 cm sealant plug is to be used to seal the biopsy tract;

FIG. 6 is a perspective view depicting an assembly of parts used in the fourth step of the novel method;

FIG. 13A is a side elevational view of a plunger having a slot formed in its distal end to form a pair of opposed arms;

FIG. 13B is a view like FIG. 13A but with the opposed arms in their open position;

FIG. 14 is a side elevational view of the plunger of FIGS. 13A and 13B but with a sleeve member added thereto, said sleeve member being in an extended position;

FIG. 15 is a side elevational view like that of FIG. 14 but with the sleeve member in its retracted configuration;

FIG. 16 is a side elevational view of a turning nut assembly for holding one end of the sealant plug;

FIG. 17 is a side elevational view showing opposite ends of the sealant plug being held on a first end by the holder of FIGS. 13A, 13B, 14, and 15 and on a second end by the holder of FIG. 16.

DETAILED DESCRIPTION

Figure 1:
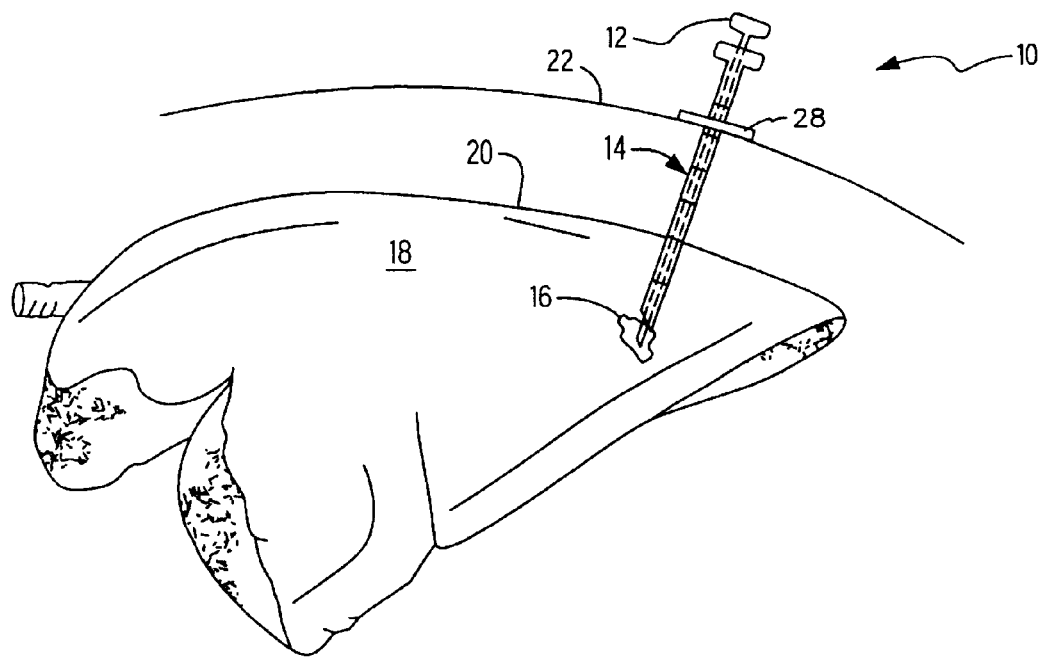
FIG. 1 is a diagrammatic view of a fine needle aspiration procedure for retrieving cellular material from a lesion.

Referring now to FIG. 1, it will there be seen that an exemplary environment where the novel method may be performed is denoted as whole by the reference numeral 10.

Fine needle aspiration (FNA) biopsy needle 12 is slideably received in coaxial needle 14 in a well-known way. A syringe attached to FNA biopsy needle 12 is not shown to simplify the drawing. FNA biopsy needle 12 is used to collect a sample of cellular material from lesion 16 from lung 18 in this illustrative embodiment. The outer surface of lung 18, known as the pleura layer, is denoted 20.

A physician, employing CT scan or other suitable measurement techniques, introduces coaxial needle 14 through the patient's skin 22, between the ribs, and into the chest cavity. Such procedure punctures lungs 18. Coaxial needle 14 is then advanced further until its leading end is positioned near lesion 16. FNA biopsy needle 12 is introduced into the lumen of coaxial needle 14 and cellular material is obtained from lesion 16. FNA biopsy needle 12 is then withdrawn from the lumen of the coaxial needle and the cellular material is delivered to a lab for analysis. Biopsy needle 12 is not used again in the procedure because the biopsy procedure has been concluded and the only task left is to seal the biopsy tract with the novel sealant plug by delivering said novel sealant plug to a precise location within the biopsy tract. Specifically, the trailing end of the sealant plug should be positioned in a range of positions between two limits where the first limit is substantially flush with the surface of the internal organ and the second limit is a distance of about 0.5 centimeters above the surface of the internal organ.

Figure 2:
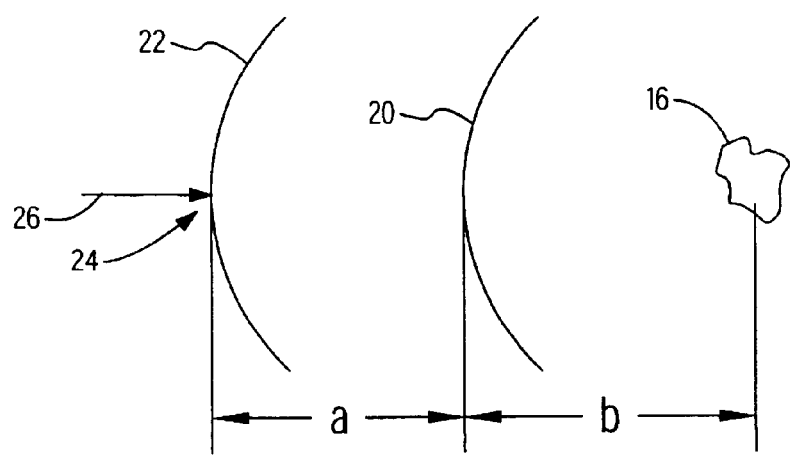
FIG. 2 is a diagrammatic view depicting a typical spacing between a skin surface, a pleural surface, and a lesion.

FIG. 2 is a diagrammatic representation of patient's skin 22 (in this case chest skin), lung surface 20 (the pleural layer), and lesion 16. The point of needle entry in skin 22 is denoted 24. The distance from said point of entry 24 to pleural layer 20 of the lung is denoted by the reference letter "a" and the distance from pleural layer 20 to lesion 16 is denoted by the reference letter "b." Distances "a" and "b" are calculated using CT imaging software. The distances are measured normally, i.e., coaxial needle 14 is positioned in normal relation to skin 22 as indicated by directional arrow 26 in FIG. 2. These measurements enable a radiologist to adjust a depth marker (not shown in FIG. 2) along the length of coaxial needle 14 prior to its insertion. As an example, where both "a" and "b" are equal to three centimeters (3 cm), the radiologist slides the marker to the six centimeter (6 cm) marker along the needle length before insertion. When the insertion is complete, the marker lies flush against the surface of the patient's skin.

Figure 3:
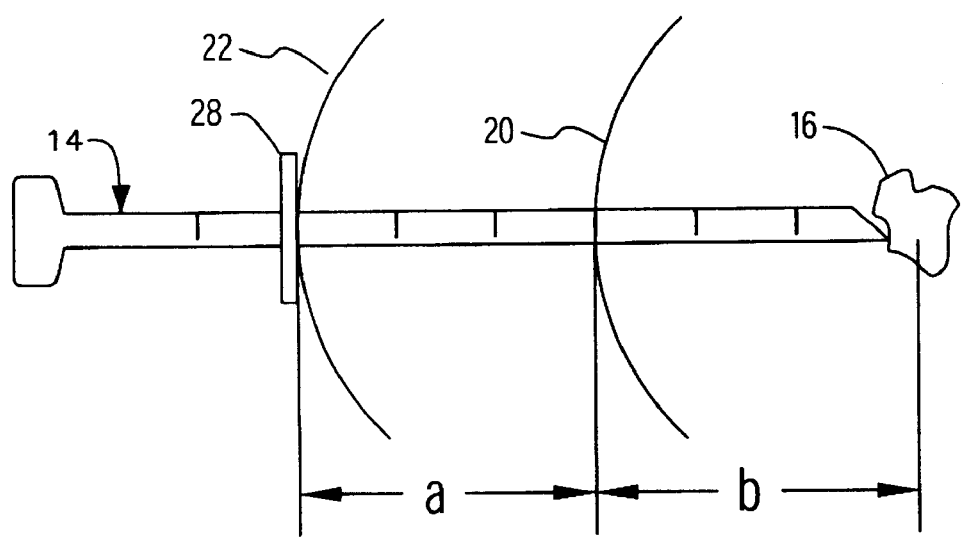
FIG. 3 is a diagrammatic view like FIG. 2, adding a coaxial needle having a marker.

In FIG. 3, marker 28 is positioned at about the sixth centimeter marker on coaxial needle 14. Distance "a" in this example is about three centimeters (3 cm) and distance "b" is about the same, making a total of six centimeters (6 cm).

Figure 4A:
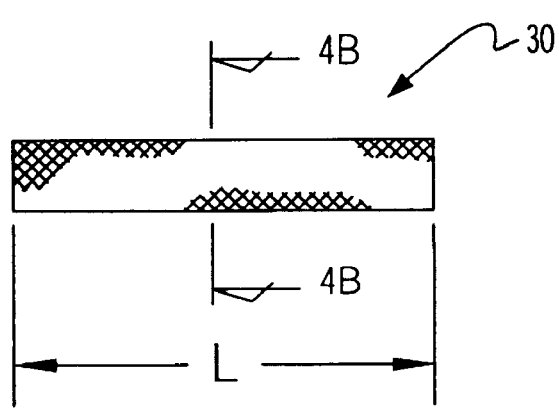
FIG. 4A is a side elevational view of a bioabsorbable sealant plug.
Figure 4B:
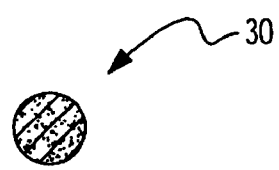
FIG. 4B is a sectional view taken along line 4B—4B in FIG. 4A.

FIG. 4A depicts a bioabsorbable plug 30 in side elevation and FIG. 4B depicts said plug in transverse cross-section. Plug 30 is designed to prevent pneumothorax in patients after a fine needle aspiration biopsy procedure. The plugs are pre-fabricated to a predetermined length, thereby eliminating any need for custom sizing for different "a" and "b" sizes.

Accordingly, for any lesion location and any needle point of entry, one-size sealant plug 30 fulfills all sealant requirements. In a preferred embodiment, the length of sealant plug 30 is two and one-half centimeters (2.5 cm).

Each plug 30 must be positioned within a biopsy tract with its proximal (trailing) end substantially flush with the pleura layer or extending outwardly from said pleura layer by a distance of about one-half centimeter (0.5 cm), or any point therebetween. This is an important feature of this invention. Where sealant plug 30 is used to seal a biopsy tract in an internal organ other a lung, the positioning is the same, i.e., the trailing end of sealant plug 30 is either flush with the surface of the internal organ or extends outwardly therefrom by a distance of 0.5 cm or less.

The novel delivery system to be disclosed hereinafter delivers the plug to its optimal position with a high level of accuracy under normal breathing conditions. The step-by-step procedure for delivery and deployment of plug 30 is as follows.

In step one (1), depicted in FIG. 5A, after a conventional biopsy procedure has been performed, coaxial needle 14 is left in the lung (having pleura 20) in the same position it was in during the procedure. During the procedure, the distal end of coaxial needle 14 is positioned at a distance equal to the sum of distances "a" and "b." Holder 28 is positioned on coaxial needle 14 so that it is in registration with the graduation marker on the coaxial needle that represents the sum of said distances "a" and "b." For example, where distance "a" is about 2.0 cm and distance "b" is about 3.0 cm, holder 28 is positioned on the 5.0 cm graduation marker and coaxial needle 14 is inserted until said holder 28 is flush with the patient's skin as depicted in FIG. 5A. This insures that the distal end of coaxial needle 14 is 5.0 cm beneath the surface of the skin, where the lesion is.

In step two (2), a predetermined distance is added to distance "a" to produce a distance "d" and coaxial needle 14 is either advanced in the direction of directional arrow 32 or retracted in the direction of arrow 34 so that its distal end is distance "d" from the surface of the patient's skin. Holder 28 is positioned on a graduation mark on the coaxial needle that represents said distance "d" and holder 28 is placed into abutting relation to the patient's skin, thereby positioning the distal end of the coaxial needle at the desired depth as depicted in FIG. 5B.

The predetermined distance is 0.5 cm less than the length of the sealant plug, in centimeters. Thus, where a sealant plug is 2.5 cm in length and where distance "a" is 2.0 cm, holder 28 is slid along the length of coaxial needle 14 until said holder is positioned at the 4.0 cm graduation markers as depicted in FIG. 5B and said holder is placed flush with the patient's skin. This positions the distal (leading) end of coaxial needle 14 four centimeters (4.0 cm) below the surface of the patient's skin and 2.0 cm below the surface of the internal organ. As will become clear as this description proceeds, a sealant plug is introduced into the lumen of coaxial needle 14 and is pushed until its leading end is substantially flush with the distal end of the coaxial needle. The sealant plug stays in place when the coaxial needle is withdrawn, the therefore the leading end of the sealant plug will remain in the biopsy tract in the internal organ but the trailing end of the sealant plug will extend or protrude from the surface of the internal organ by about 0.5 centimeters.

Figures 6A, 7:
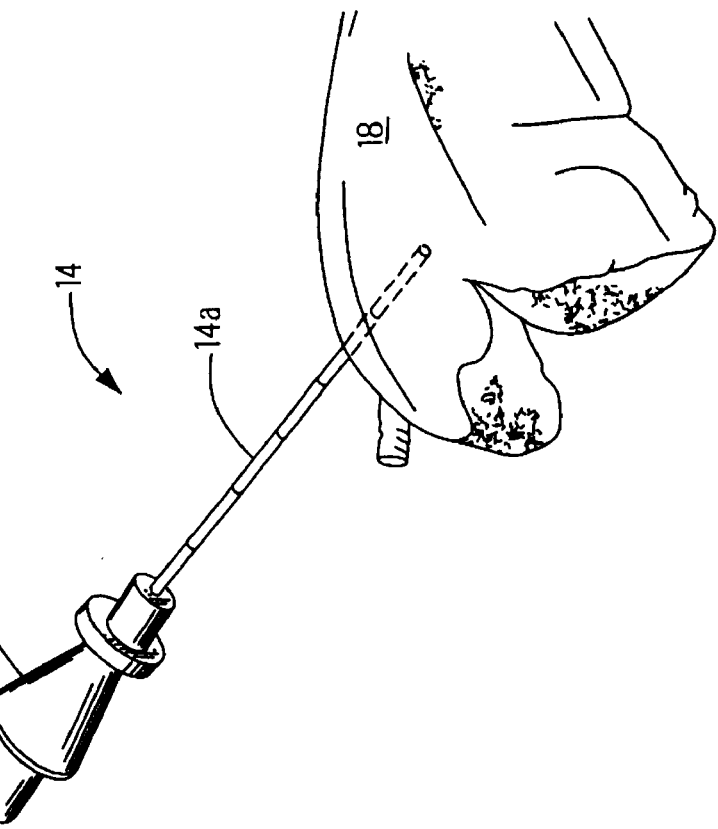
FIG. 7 is a perspective view depicting the parts used in the sixth step.

The next step, as best understood in connection with FIG. 6, requires that supporting leg 36 and plunger 38 be assembled as indicated and adjusted in accordance with a chart, depicted in FIG. 6A, that is provided to the end user, said chart being provided as a part of a package including instructions for use of the novel tool. The chart provides the plunger-to-supporting leg ratio with respect to measurement of distance "a." Graduation markings in centimeters are provided along the extent of supporting leg 36 and plunger 38.

In the next step, plunger 38 is locked into position relative to supporting leg 36 by advancing locking screw 40 in a well-known way. When locked to one another, supporting leg 36 and plunger 38 form an assembly that moves as a single unit.

As indicated in FIG. 7, sealant plug 30 is then introduced into coaxial needle 14 through the trailing end of a luer connector 42. A special holder for holding plug 30 during this procedure is not shown. A pair of tweezers could also be used as the holder.

Figure 8:
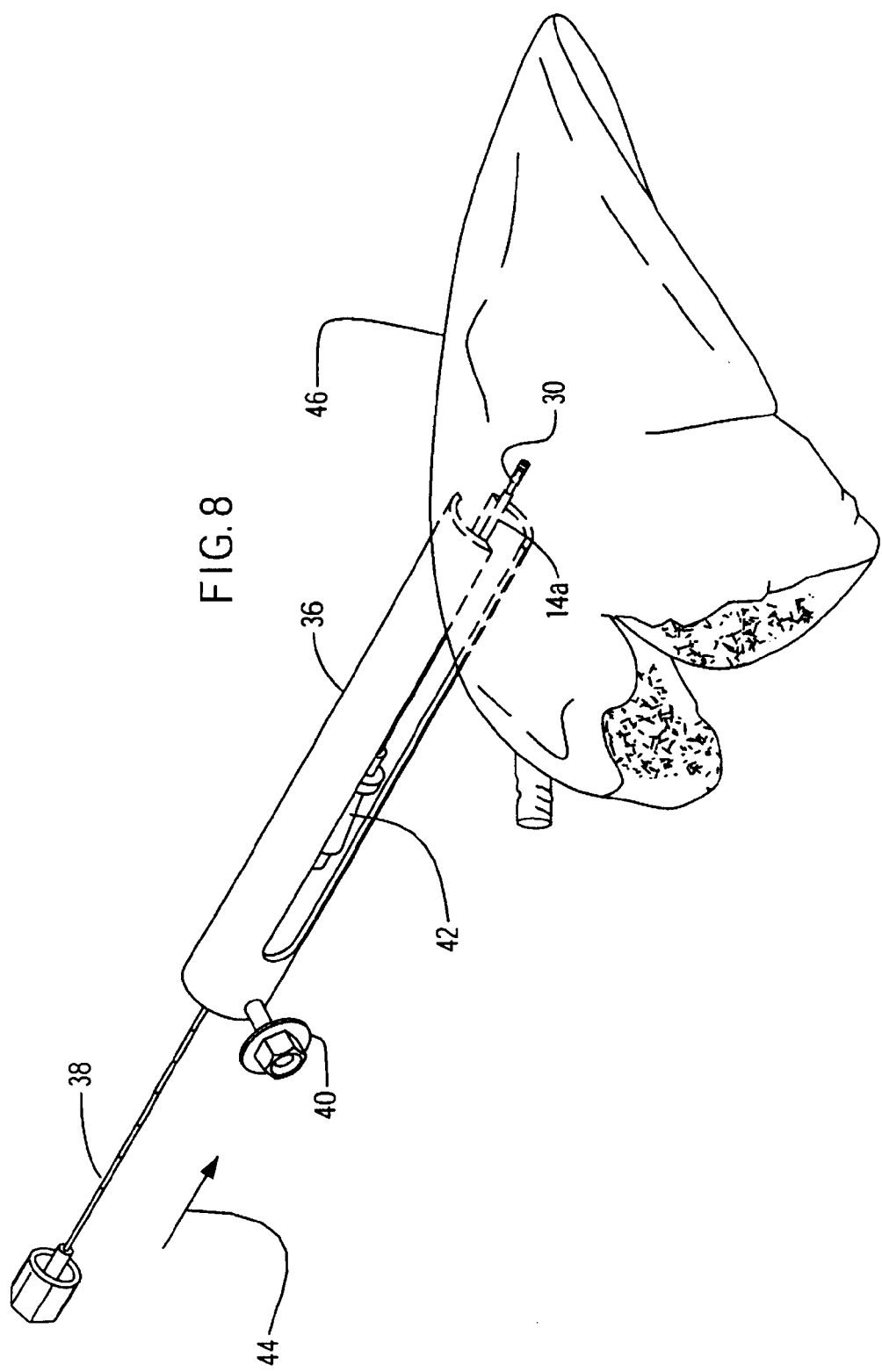
FIG. 8 is a perspective view of the parts used in the seventh step.

In the next step, depicted in FIG. 8, the supporting leg 36/plunger 38 assembly is positioned as shown. Specifically, the leading end of plunger 38 is introduced into the trailing end of the lumen of coaxial needle 14, thereby advancing sealant plug 30 in a trailing-to-leading direction, towards the distal end of coaxial needle 14.

Plunger 38 and sealant plug 30 are advanced within said lumen of coaxial needle 14 until supporting leg 36 abuts the patient's skin and is stopped thereby.

Plunger 38 and sealant plug 30 travel together as a unit as aforesaid, so plunger 38 stops traveling in said trailing-to-leading direction when supporting leg 36 abuts the patient's tissue. At that time, sealant plug 30 is positioned at the distal end of the plunger but is still housed within coaxial needle 14 as depicted in FIG. 8. Specifically, the leading end of sealant plug 30 is flush with the distal end of coaxial needle 14.

Figure 9:
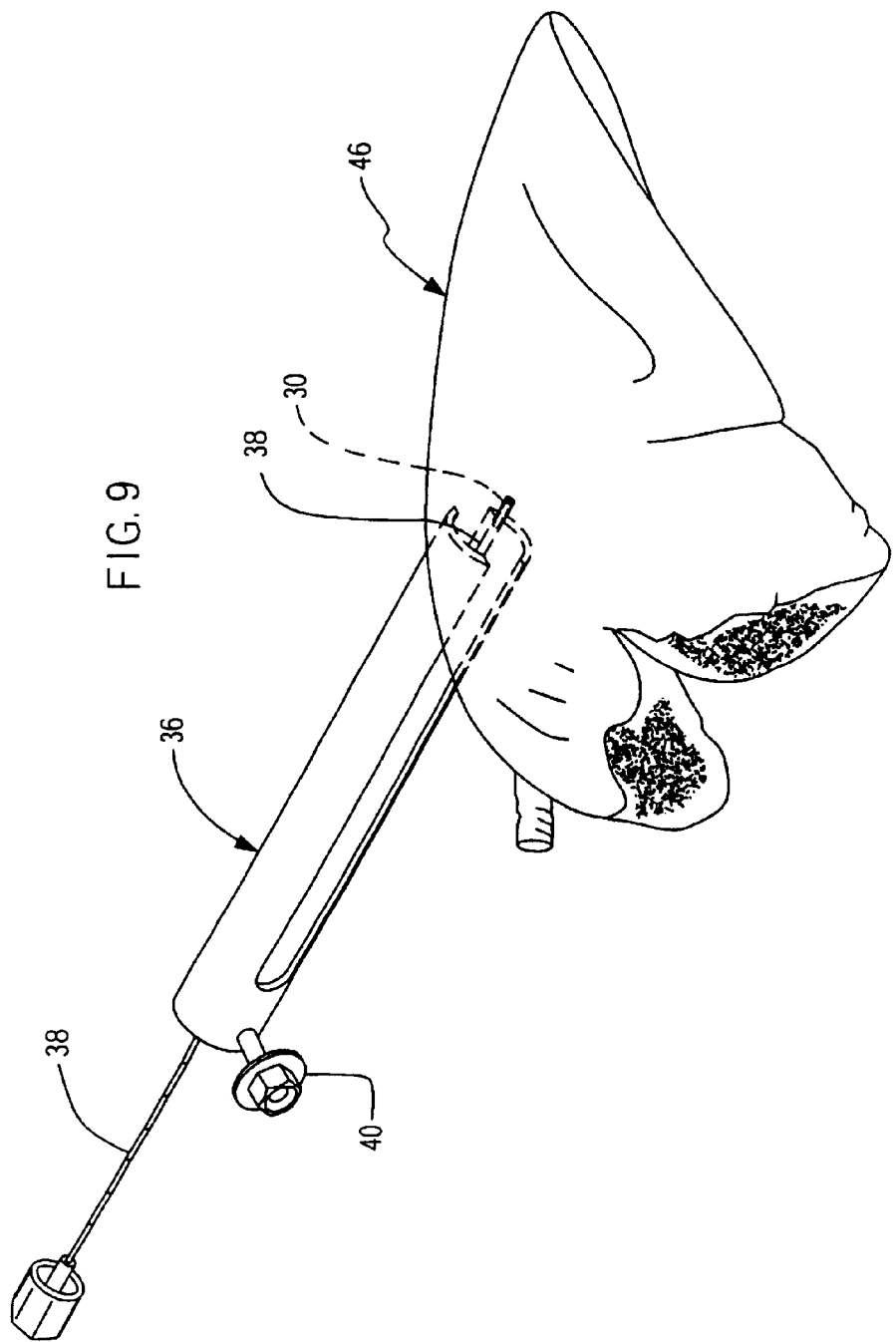
FIG. 9 is a perspective view of the parts used in the ninth step.

Coaxial needle 14 is then removed from the biopsy tract (i.e., it is withdrawn from the body of the patient). Supporting leg 36 and plunger 38 are maintained in their FIG. 9 position. This deploys sealant plug 30 into the biopsy tract at the exact position depicted in FIG. 9. In other words, when coaxial needle 14 is withdrawn, plunger 38 prevents withdrawal of plug 30, holding said plug 30 in position so that withdrawal of coaxial needle 14 leaves said plug 30 in said biopsy tract at the desired location in lung 46.

Figure 10:
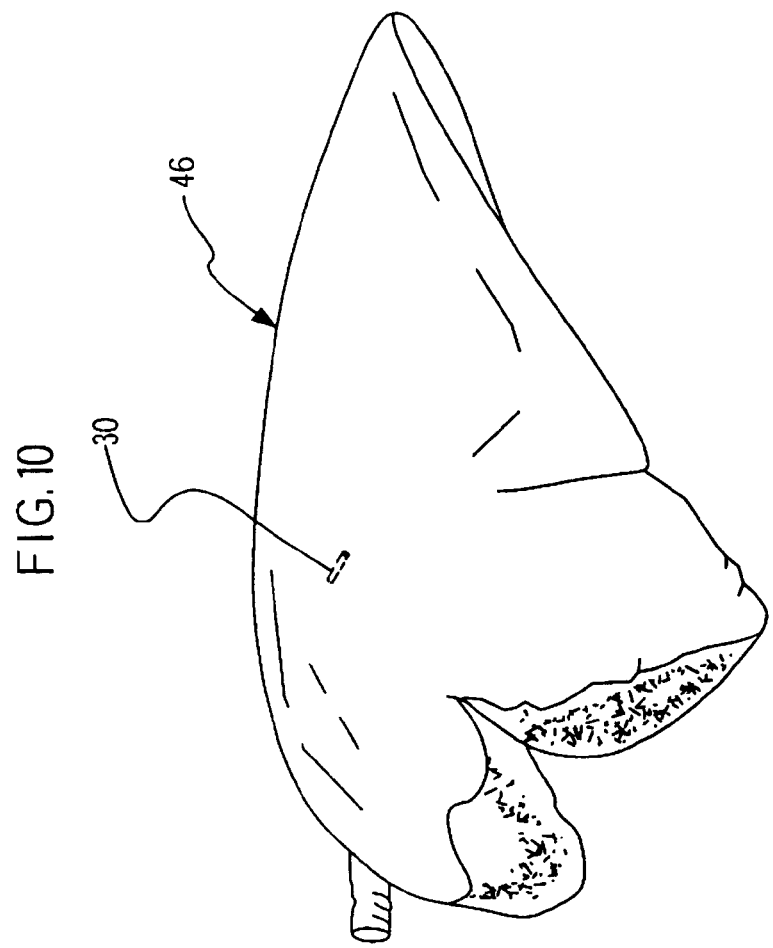
FIG. 10 is a diagrammatic perspective view of a lung having the sealant plug positioned therewithin as a result of the tenth and final step of the first embodiment.

In the final step, supporting leg 36 and plunger 38 are withdrawn, leaving sealant plug 30 in lung 46 at the desired position as depicted in FIG. 10.

Figure 11:
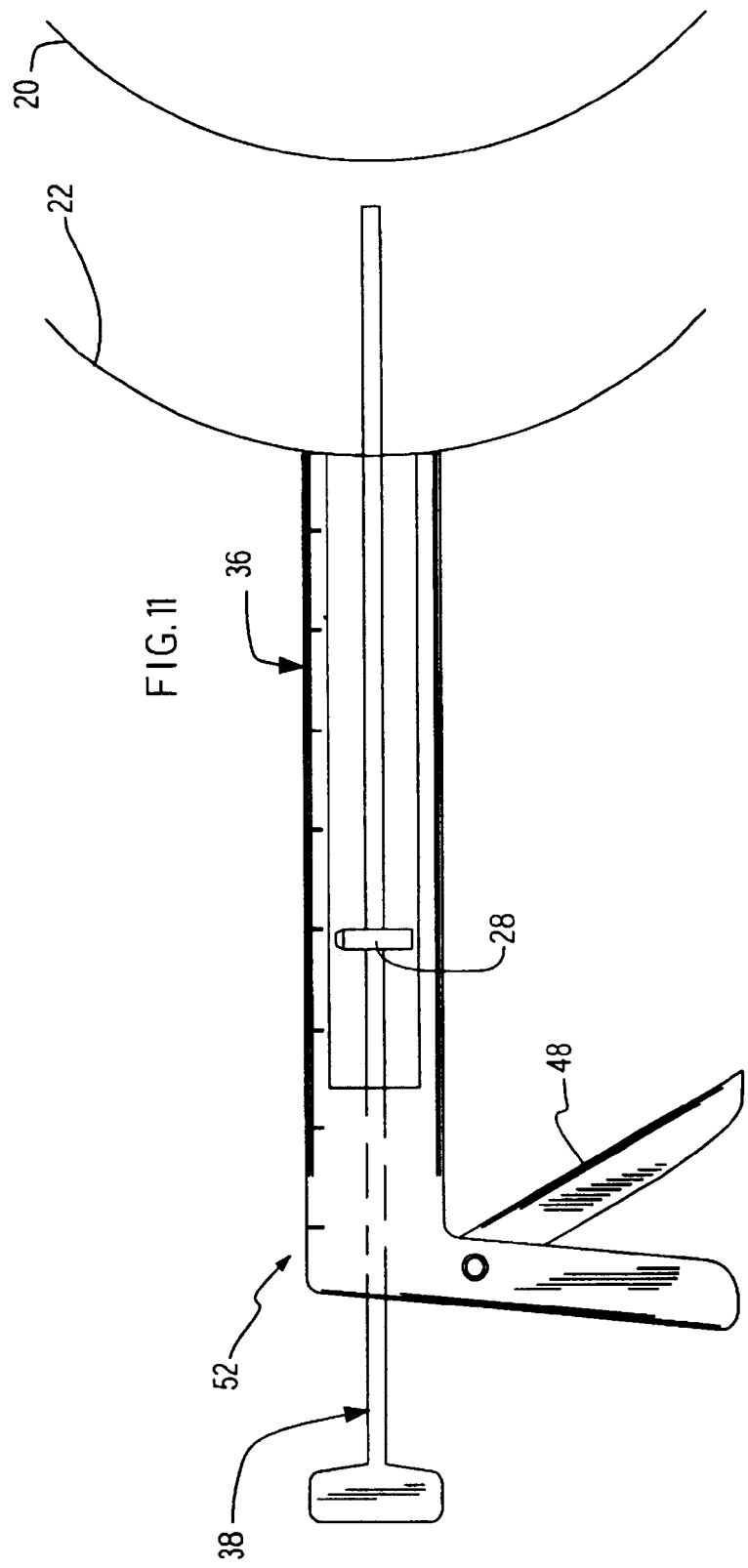
FIG. 11 is a diagrammatic, side elevational view of a second embodiment of the novel delivery system.

FIG. 11 depicts a second embodiment 50 of the novel delivery system. Supporting leg 36 is provided in the form of a pistol grip body that includes a trigger 48.

Operation of delivery system 50 is much like that of a caulk dispensing gun. When pivotally-mounted trigger 48 is pulled, plunger 38 is free to be advanced or withdrawn relative to supporting leg 36, i.e., pulling trigger 48 releases plunger 38 so that it may be manually re-positioned. When trigger 48 is released, plunger 38 is locked into position relative to supporting leg 36. Thus, trigger 48 when released functions like locking screw 40. Plunger 38 and supporting leg 36 therefore become one unit as in the first embodiment.

Graduation markers 52 are imprinted, notched, or otherwise affixed to supporting leg 36 as depicted. Holder 28 is mounted upon plunger 38. The chart referred to in the disclosure of the first embodiment is consulted and plunger 38 and supporting leg 36 are positioned relative to one another in accordance with the CT scan measurement-based chart of FIG. 6A. In FIG. 11, holder 28 is positioned at the 4th graduation marker.

For example, suppose a particular CT scan measurement is made and the distance from the surface of the patient's skin to the internal organ (distance "a") is determined to be 3.0 cm. That measurement is looked up in the chart of FIG. 6A and the chart says to set marker 28 on the "$4^{th}$ notch." Trigger 48 is pulled to release plunger 38 and said plunger is withdrawn or retracted until holder 28 is aligned with the fourth graduation marker. That particular setting is depicted in FIG. 11. Trigger 48 is then released to lock plunger 38 into the selected position.

Figure 12:
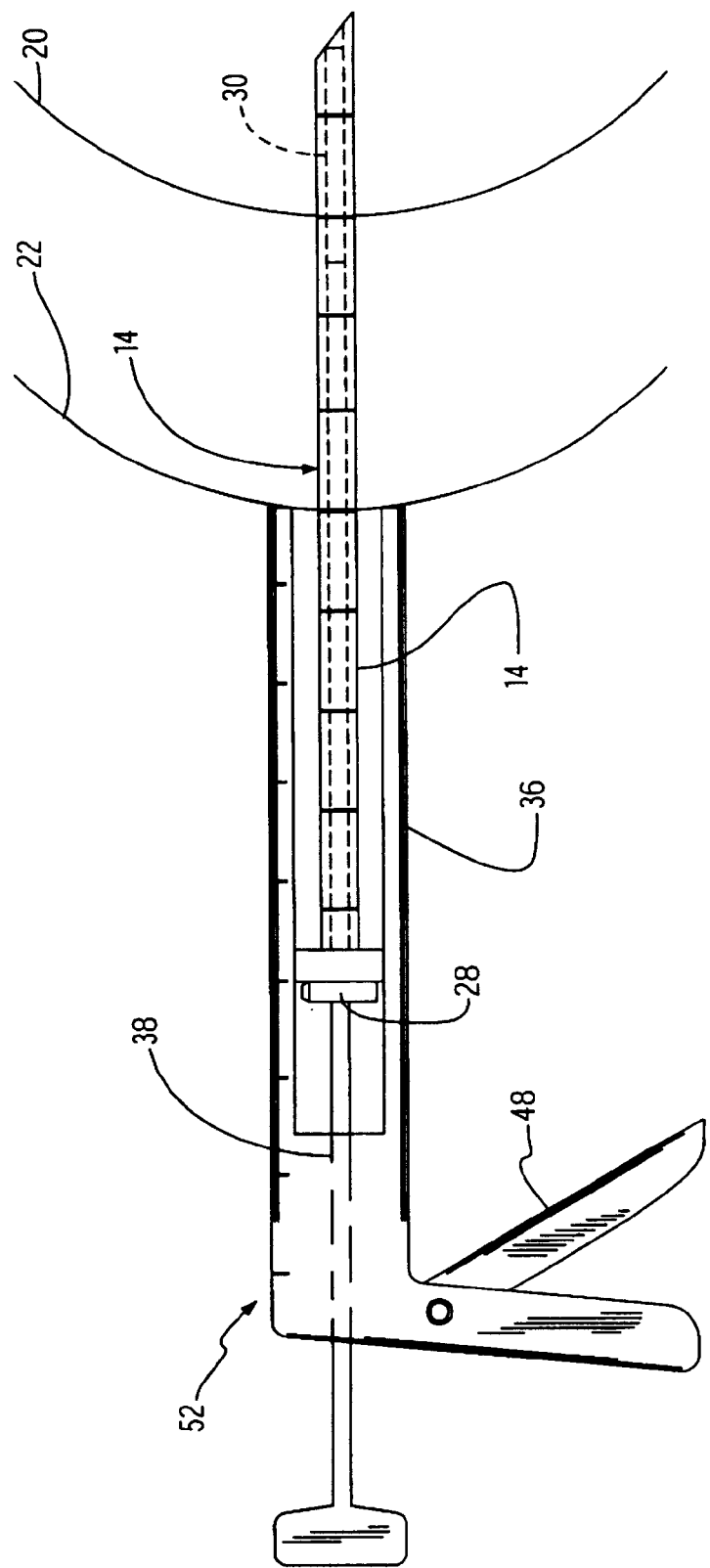
FIG. 12 is a view like that of FIG. 11 but with the coaxial needle in its extended position.

FIG. 12 depicts a structure much like the structure of FIG. 11, but includes coaxial needle 14 and plug 30 as well.

Just as in the first embodiment, sealant plug 30 is introduced into the lumen of coaxial needle 14 at the trailing end thereof with a suitable holding tool, and the leading end of plunger 38 is used to push sealant plug 30 toward the distal end of coaxial needle 14. When the leading end of supporting leg 36 abuts the patient's skin, the leading end of sealant plug 30 is flush with said distal end of coaxial needle 14 as depicted in FIG. 12. Coaxial needle 14 is then withdrawn from pleura 20 and skin 22 while the position of plunger 38 is maintained. This ensures that plug 30 is implanted at the optimal location, i.e., with about a half centimeter of the trailing end thereof protruding out of the internal organ. The plunger/supporting leg assembly is then withdrawn to complete the procedure.

Plunger 38 does not fully occupy the lumen of coaxial needle 14 because the outer diameter of the plunger is less than the diameter of the lumen. Accordingly, a saline solution or other suitable substance, which may take the form of a liquid fluid, a powder, or other substance, may be introduced into the coaxial needle lumen, from the trailing end thereof, so that it flows around plunger 38 and reaches sealant plug 30. Such substance is selected to begin or accelerate hydration of sealant plug 30. Thus, expansion of sealant plug 30 does not rely entirely on the presence of bodily fluid in the patient. Moreover, the trailing end of sealant plug is most affected by said substance, as is desired because it is the trailing end that extends beyond the surface of the internal organ within which the biopsy procedure was performed. Such prehydration may be desireable when sealing a lung biopsy tract.

Contrast agents may be added as well to the saline solution or other expansion stimulant to improve visibility of the sealant plug installation under CT scan.

Those skilled in the art of machine design, having seen the first two embodiments of this invention, will now be aware of numerous other ways to accomplish the precise positioning of sealant plug 30 as disclosed herein. All obvious variation of the disclosed embodiments are within the scope of this invention.

In a third embodiment, plunger 38a (FIG. 13) is provided in the form of a tube having slot 54 formed in its distal end, thereby forming bifurcated ends that may be spread apart from one another. The inside diameter of tube 38a is smaller than the outside diameter of sealant plug 30. Significantly, plunger 38a is formed of a flexible and resilient material with memory, such as nitinol, so that slot 54 may be opened as at 56 in FIG. 13B.

When the distal end of plunger 38a is opened as at 56 by spreading said ends apart, the trailing or proximal end of bioabsorbable sealant plug 30 is then positioned between said open ends as indicated by assembly arrow 58 in FIG. 13B.

As depicted in FIG. 14, sleeve 60 is then advanced in a trailing-to-leading direction, thereby closing the distal end of plunger 38 until it returns to its FIG. 13A position where it clamps down on plug 30. Sleeve 60 is omitted from FIGS. 13A and 13B to simplify said Figures.

When sleeve 60 is retracted as depicted in FIG. 15, the opposed ends of slotted distal end 56 return to their FIG. 13B configuration under their inherent bias, thereby releasing the proximal or trailing end of plug 30. Plunger 38a and sleeve 60 are then withdrawn, leaving plug 30 in the biopsy tract at a specific, preselected location. The procedure of the first two embodiments, relating to the initial placement of the distal end of coaxial needle 14 at a depth equal to distance "a" plus distance "b" to facilitate the biopsy procedure, followed by adjustment of the depth of said distal end by adding a predetermined distance to distance "a," and the other steps as aforesaid, are also followed in this third embodiment. Coaxial needle 14 is not illustrated in this embodiment to simplify the drawings.

A fourth embodiment is disclosed in FIGS. 16 and 17. Holder 62 in FIG. 16 includes threaded turning nut 64 having a general "E" shape. Holder 64 further includes leading end 66 that advances in a trailing-to-leading direction, as indicated by single-headed directional arrow 68, when turning nut 64 is screw-threadedly advanced. The external surface of housing 70 is complementally threaded to engage said turning nut 64.

Longitudinally-extending throughbore 72 is formed in housing 70 and extends therethrough from the trailing to the leading end thereof. The trailing end of bore 72 accommodates leading end 66 of turning nut 64. Flat washer 74 is positioned in leading relation to leading end 66 and said flat washer is therefore constrained to displace in a trailing-to-leading direction, indicated by said directional arrow 68, when turning nut 64 is advanced.

Silicon gasket 76 of frusto-conical configuration is positioned in leading relation to flat washer 74 and is also constrained to advance in the direction indicated by arrow 68 when turning nut 64 is advanced.

Throughbore 72 has a diameter-reducing taper 72a formed therein and a reduced diameter leading end 72b. As turning nut 64 is advanced, leading end 66 thereof bears against flat washer 74 and said flat washer 64 bears against the trailing end of silicon gasket 76, driving it into reduced diameter leading section 72b of throughbore 72. Diameter-reducing taper 72a serves to gradually compress silicon gasket 76 into said leading section 72b as said turning nut 64 is advanced.

Flat washer 74 and silicon gasket 76 are centrally apertured and receive the trailing end of plug 30 therewithin. Accordingly, said trailing end of plug 30 is compressed as silicon gasket 76 is driven into reduced diameter bore 72b, thereby locking down on that part of plug 30 disposed within the central aperture or bore of silicon gasket 76.

FIG. 17 illustrates how holder 38a of FIGS. 13A, 13B, 14, and 15 may be used with turning nut 64 to apply tension to plug 30. The opposite ends of said plug 30 are grasped by said respective plug holders and said plug holders are pulled away from one another as indicated by double-headed directional arrow 78. The tensile force applied to plug 30 may be controlled to a preselected tensile force by relative movement of said plug holders by a preselected distance. The tensile force so applied provides residual stress in plug 30 before it is delivered to a site and deployed from coaxial needle 14 so that said plug expands more quickly when subjected to a stimulus such as moisture than it would have expanded if it had not been subjected to such tensile force.

After plug 30 has been stretched in the manner indicated in FIG. 17, or by some other, equivalent manner, one end thereof is released so that the plug may be delivered to a biopsy tract that requires plugging. In this particular example, turning nut 64 is released from plug 30 and said plug remains in the grip of plunger 38a. It is then delivered to the site as described in connection with the third embodiment.

Figure 18:
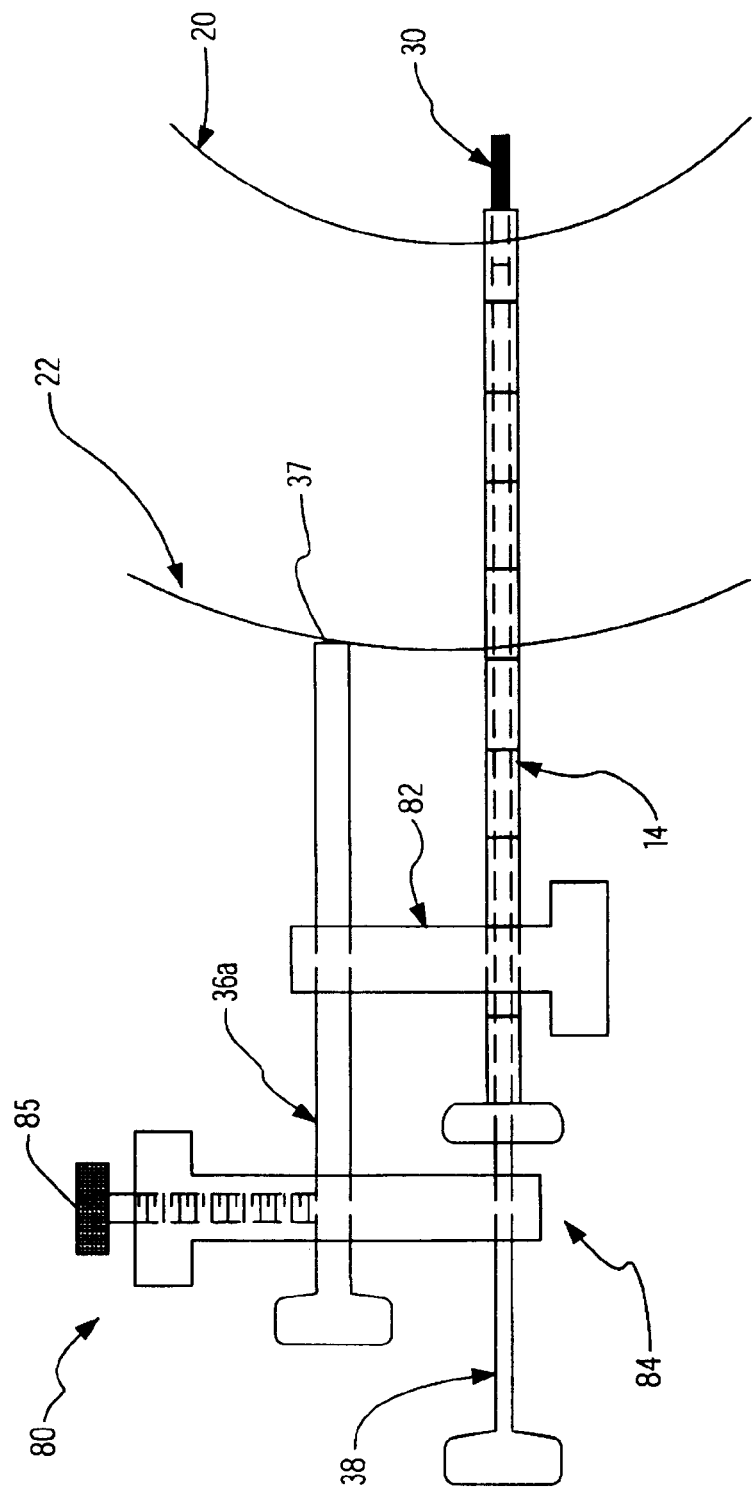
FIG. 18 is a side elevational view of a tool that maintains a supporting rod against a patient's skin surface while holding a plunger and coaxial needle assembly in parallel relation to said supporting rod.

A fifth embodiment is denoted 80 as a whole in FIG. 18. Supporting rod 36a is employed in this embodiment, in lieu of supporting leg 36 of the first embodiment. Positioning adaptor 82 guides supporting rod 36a with respect to coaxial needle 14. Similarly, supporting rod 36a and plunger 38 are interconnected to one another by supporting adapter 84. Locking screw 85 locks supporting adapter 84 to supporting rod 36a.

The distance between skin 22 and lung 20 is determined by CT scanner or other suitable means. Based upon that measured distance, the relative positioning of supporting rod 36a and plunger 38 are adjusted and locked accordingly as in the earlier-described embodiments. Plunger 38 and supporting rod 36a are then inserted through coaxial needle 14 and positioning adapter 82.

Supporting rod 36a has a flat, atraumatic distal end 37 that rests against skin 22. Plunger 38 is positioned in trailing relation to sealant plug 30 when supporting rod 36a comes to rest against skin 22, and the leading end of sealant plug 30 is flush with the distal end of coaxial needle 14 as in the earlier embodiments.

Supporting rod 36a is held in place while coaxial needle 14 is withdrawn from the biopsy tract. Supporting rod 36a and plunger 38 are then removed, leaving sealant plug 30 optimally positioned in the biopsy tract with its trailing end extending from the internal organ by a distance between 0.0 to 0.5 cm.

In all of the embodiments disclosed herein, the sealant plug is understood to expand both radially and longitudinally upon coming into contact with blood or other bodily fluids or upon contact with a saline solution or other expansion-enhancing substance. However, in some applications a longitudinal expansion may be undesireable. For example, foreshortening in arterial stents such as a Wall® stent causes misplacement of the stent at the right target location. Longitudinal expansion of a sealant plug can cause the plug to move away from the target. By inducing a certain amount of stress, a dehydrated sealant plug could be increased in length prior to hydration so that subsequent hydration of the plug causes radial expansion only. This is achieved by balancing the residual stress induced in the plug to achieve a very small longitudinal expansion. With increasingly refined techniques, the expansion approaches a zero percent (0%) length expansion.

The ability to cause a rapid rate of hydration due to different levels of residual stress induced in a dehydrated plug can be harnessed to control drug release rates when different drugs are diluted with polymers. The polymers may be soluble or insoluble, biodegradable or nonbiodegradable, and natural or synthetic. Polymers may be therapeutic themseleves or they may be used to deliver therapeutic agents. Polymers may be provided to minimize inflammation or to promote inflammation as may be desired for a particular procedure. They may be chosen to suppress secondary bleeding and late fibrotic scarring. Polymers may also be selected to promote angiogenic and fibrogenic responses, and so on.

Different hydrogel-base polymers may also be used for such applications as well, including hydrogels, thermoplastics, homopolymers, copolymers or blends, natural or synthetic. A hydrogel is an aqueous phase having an interlaced polymeric component, prepferably ninety per cent (90%) water by weight. A hydrogel may also be defined as a colloid in which the disperse phase (colloid) has combined with the continuous phase (water) to produce a viscuous, jelly-like product. Poly(oxyalkene) polymers and copolymers such as poly(ethylene oxide)-poly(propylene oxide) copolymers, and copolymers and blends of these polymers with polymers such as poly(alpha-hydroxy acids), including but not limited to lactic, glycolic and hydroxybutyric acids, polycaprolactones, and polyvalerolactones, can be synthesized or commercially obtained.

Polymers may be themselves bioactive or contain embedded or grafted bioactive molecules, peptides, lipids, drugs, or other moities. Such polymers may suppress, maintain or stimulate a biological response.

By controlling the rate of expansion, the rate of drug delivery is also controlled. Faster hydration rates, for example, provide faster dilution of drugs.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A method for delivering a sealant plug to an optimal position within an internal organ with a high degree of accuracy, comprising the steps of:

measuring a first distance defined as the distance between a patient's skin surface and the surface of an internal organ having a lesion therein;

inserting a coaxial needle through said patient's skin surface to a predetermined depth such that a distal end of said coaxial needle is positioned adjacent said lesion;

inserting a biopsy needle into a lumen of said coaxial needle and performing a biopsy procedure;

removing the biopsy needle from said lumen upon completion of said biopsy procedure;

leaving the coaxial needle in said biopsy tract in the same position said coaxial needle was in during the biopsy procedure;

advancing or retracting said coaxial needle so that the distal end of said coaxial needle is positioned at a depth beneath said skin surface by a distance that is calculated by adding a predetermined distance to said first distance;

providing a supporting leg and a plunger having graduation marks thereon;

connecting the supporting leg and a plunger to one another to form a plunger/supporting leg assembly;

adjusting said plunger relative to said supporting leg in accordance with a chart containing predetermined settings, said chart including a different plunger-to-supporting leg setting for different measurements of said first distance;

locking said plunger into position relative to said supporting leg so that said plunger/supporting leg assembly is a unitary assembly;

introducing a sealant plug into said coaxial needle through the trailing end of said coaxial needle;

ensleeving said coaxial needle within said supporting leg;

introducing a leading end of said plunger into the trailing end of the lumen of said coaxial needle;

advancing said plunger in a trailing-to-leading direction through said lumen towards said internal organ, thereby pushing said sealant plug towards said distal end of said coaxial needle;

advancing said plunger and sealant plug within said lumen of said coaxial needle until said supporting leg abuts the patient's skin and is stopped thereby, said sealant plug having a leading end positioned flush with the distal end of said coaxial needle when said supporting leg abuts said patient's skin;

withdrawing said coaxial needle from said biopsy tract while maintaining said supporting leg and said plunger in their respective positions, thereby deploying said sealant plug into said biopsy tract;

withdrawing said supporting leg and said plunger, leaving said sealant plug in said internal organ at a preselected position.

2. The method of claim 1, further comprising the steps of:

measuring a second distance between the surface of said internal organ and said lesion;

adding said first distance and said second distance to one another to obtain a third distance that represents the depth of said lesion beneath the surface of said patient's skin;

positioning said distal end of said coaxial needle at said third distance below the surface of the patient's skin prior to the step of introducing said biopsy needle into the lumen of said coaxial needle.

3. The method of claim 2, further comprising the steps of:

forming a plurality of graduation markers along an extent of said coaxial needle;

providing a holder that is movably adjustable along the extent of said coaxial needle;

prior to the step of positioning said distal end of said coaxial needle at said third distance below the surface of the patient's skin, positioning said holder on a graduation marker that represents said third distance; and inserting said coaxial needle until said distal end of said coaxial needle is positioned said third distance below the surface of said patient's skin by positioning said holder in abutting relation to said surface of said patient's skin.

4. The method of claim 1, further comprising the step of:

calculating said predetermined distance my measuring the longitudinal extent of said sealant plug and subtracting about one-half a centimeter from said longitudinal extent;

whereby a trailing end of said sealant plug protrudes from said surface of said internal organ by a distance of about one-half a centimeter when the steps of the method are completed.

5. The method of claim 1, further comprising the step of:

providing said supporting leg in generally cylindrical form;

capping a trailing end of said supporting leg and providing a central aperture in said cap, said central aperture adapted to slidingly receive said plunger;

positioning said plunger relative to said supporting leg in accordance with said chart by slideably introducing said plunger through said central aperture until a graduation marking on said plunger identified by said chart is flush with said trailing ed of said supporting leg.

6. The method of claim 5, further comprising the steps of:

forming a radial opening in said supporting leg;

providing a locking screw that extends through said radial opening; and locking said plunger relative to said supporting leg by advancing said locking screw so that a distal end thereof bears against said plunger.

7. The method of claim 1, further comprising the step of:

introducing a hydrating means into said lumen of said coaxial needle before the step of withdrawing said coaxial needle so that said sealant plug begins re-hydrating prior to said withdrawal of said coaxial needle.

8. The method of claim 1, further comprising the steps of:

providing said plunger in hollow form so that it has a lumen of sufficient diameter to receive a hydrating means; and introducing a hydrating means into said lumen of said plunger before the step of withdrawing said plunger so that said sealant plug begins re-hydrating prior to said withdrawal of said plunger.

9. A method for delivering a sealant plug to an optimal position within an internal organ with a high degree of accuracy, comprising the steps of:

measuring a first distance defined as the distance between a patient's skin surface and the surface of an internal organ having a lesion therein;

inserting a coaxial needle through said patient's skin surface to a predetermined depth such that a distal end of said coaxial needle is positioned adjacent said lesion;

inserting a biopsy needle into a lumen of said coaxial needle and performing a biopsy procedure;

removing the biopsy needle from said lumen upon completion of said biopsy procedure;

leaving the coaxial needle in said biopsy tract in the same position said coaxial needle was in during the biopsy procedure;

advancing or retracting said coaxial needle so that the distal end of said coaxial needle is positioned at a depth beneath said skin surface by a distance that is calculated by adding a predetermined distance to said first distance;

providing a supporting leg in the form of a pistol grip body that includes a pivotally-mounted trigger;

mounting a plunger to said supporting leg such that said plunger may be advanced or withdrawn when said trigger is pulled and so that said plunger is locked into position relative to said supporting leg when said trigger is released;

providing graduation markings along the extent of said supporting leg;

slideably mounting a marker on said plunger;

connecting the supporting leg and a plunger to one another to form a plunger/supporting leg assembly;

adjusting said plunger relative to said supporting leg in accordance with a chart containing predetermined settings, said chart including a different plunger-to-supporting leg setting for different measurements of said first distance;

aligning said marker on said plunger with a graduation marking on said supporting leg in accordance with a setting provided by said chart;

locking said plunger into position relative to said supporting leg, by releasing said trigger, so that said plunger/supporting leg assembly is a unitary assembly;

introducing a sealant plug into the lumen of said coaxial needle at the trailing end thereof;

introducing said plunger into said trailing end of said coaxial needle and pushing said plunger in a trailing-to-leading direction to thereby advance said sealant plug towards said distal end of said coaxial needle;

completing said introducing step when a leading end of said supporting leg abuts said patient's skin, said sealant plug having a leading end flush with the distal end of said coaxial needle when said introducing step is completed;

withdrawing said coaxial needle from said internal organ and from said patient's body while maintaining the position of said plunger; and withdrawing said plunger/supporting leg assembly;

whereby optimal positioning of said sealant plug is obtained.

10. A method for delivering a sealant plug to an optimal position within an internal organ with a high degree of accuracy, comprising the steps of:

providing a plunger in the form of a tube having a slot formed in its distal end so that said distal end is bifurcated into two arm members;

configuring an inside diameter of said tube so that said inside diameter is smaller than an outside diameter of said sealant plug;

forming said plunger from a flexible and resilient material with memory so that said arms may be spread apart from one another;

spreading said arms apart from one another and positioning a trailing end of said sealant plug between said open arms;

ensleeving said tube in a sleeve member and advancing said sleeve member in a trailing-to-leading direction, thereby causing said arms to close with respect to one another where said arms clamp down on said sealant plug;

positioning said sealant plug at a predetermined optimal position;

retracting said sleeve member so that said arms spread apart from one another under their inherent bias, thereby releasing said sealant plug at said optimal position;

withdrawing said plunger and said sleeve member while leaving said sealant plug in said optimal position.

11. A method for holding a sealant plug, comprising the steps of:

providing a cylindrical housing having screw threads formed on an external surface thereof and having a longitudinally-extending throughbore formed therein;

providing a screw-threaded turning nut that screw-threadedly engages the screw threads formed in said external surface of said cylindrical housing;

said turning nut having a general "E" shape where a central hub of said turning nut includes a leading end that extends into a trailing end of said bore formed in said cylindrical housing;

positioning a centrally apertured flat washer in leading relation to said leading end so that said flat washer is constrained to displace in a trailing-to-leading direction when said turning nut is advanced;

positioning a flexible and resilient gasket of frusto-conical configuration and having a central throughbore formed therein in leading relation to said flat washer so that flexible and resilient gasket is also constrained to displace in a trailing-to-leading direction when said turning nut is advanced;

forming a diameter-reducing taper in said longitudinally-extending throughbore so that said throughbore has a reduced diameter leading end;

advancing said turning nut so that said leading end thereof bears against said flat washer and said flat washer bears against the trailing end of said flexible and resilient gasket, driving said gasket into said reduced diameter leading end of said throughbore;

said diameter-reducing taper serving to gradually compress said flexible and resilient gasket into said reduced diameter leading section as said turning nut is advanced;

positioning the trailing end of said sealant plug within the central aperture of said flat washer and the central throughbore of said flexible and resilient gasket so that said trailing end of said sealant plug is compressed as said flexible and resilient gasket is driven into said reduced diameter bore, thereby locking down on that part of said sealant plug disposed within said flat washer central aperture and central bore of said flexible and resilient gasket.

12. A method of pre-stressing a dehydrated sealant plug so that it hydrates at a faster rate than a dehydrated sealant plug that has not been pre-stressed, comprising the steps of:

grasping a first end of said sealant plug with a first holder;

grasping a second end of said sealant plug with a second holder; and separating said holders from one another to apply tension to said sealant plug.

13. A method for delivering a sealant plug to an optimal position within an internal organ with a high degree of accuracy, comprising the steps of:

providing a supporting rod having a flat, atraumatic distal end adapted to rest against a patient's skin surface;

providing a coaxial needle having a lumen;

providing a positioning adaptor and interconnecting said supporting rod and said coaxial needle to one another with said positioning adaptor so that said supporting rod is disposed in parallel relation said coaxial needle;

providing a plunger adapted to be slideably received within said lumen of said coaxial needle;

providing a supporting adaptor and interconnecting said supporting rod and said plunger to one another with said supporting adapter;

locking said supporting adapter to said supporting rod;

employing an imaging means to determine a distance between the patient's skin surface and the surface of an internal organ;

adjusting the relative positioning of said supporting rod and said plunger based upon said measured distance, and locking said supporting rod and plunger into position;

introducing a sealant plug into a lumen of said coaxial needle;

advancing said plunger in a trailing-to-leading direction through said lumen of said coaxial needle, thereby pushing said sealant plug toward a distal end of said coaxial needle;

completing said introducing step when a leading end of said supporting leg abuts said patient's skin surface, said sealant plug having a leading end flush with the distal end of said coaxial needle when said introducing step is completed;

withdrawing said coaxial needle from said internal organ and from said patient's body while maintaining the position of said plunger; and withdrawing said plunger and supporting leg, leaving said sealant plug optimally positioned in the biopsy tract.

* * * * *